(12) United States Patent
Patzek, IV (10) Patent No.: US 9,907,460 B2
(45) Date of Patent: Mar. 6, 2018

(54) ENDOSCOPE CLEANING BRUSH APPARATUS

(71) Applicant: Michael J. Patzek, IV, Quakertown, PA (US)

(72) Inventor: Michael J. Patzek, IV, Quakertown, PA (US)

( * ) Notice: Subject to any disclaimer, the term of this patent is extended or adjusted under 35 U.S.C. 154(b) by 36 days.

(21) Appl. No.: 15/209,056

(22) Filed: Jul. 13, 2016

(65) Prior Publication Data

US 2017/0020380 A1    Jan. 26, 2017

Related U.S. Application Data

(60) Provisional application No. 62/191,718, filed on Jul. 13, 2015.

(51) Int. Cl.
*B08B 7/00* (2006.01)
*A61B 1/12* (2006.01)
(Continued)

(52) U.S. Cl.
CPC .............. *A61B 1/122* (2013.01); *A46B 5/002* (2013.01); *A61B 1/125* (2013.01); *B08B 1/00* (2013.01);
(Continued)

(58) Field of Classification Search
CPC ........... A61B 1/22; A61B 1/125; A46B 5/002; B08B 1/00; B08B 1/002; B08B 1/006; B08B 9/00
See application file for complete search history.

(56) References Cited

U.S. PATENT DOCUMENTS

| 1,742,497 A | 1/1930 | Dickinson |
| 4,288,882 A | 9/1981 | Takeuchi |
(Continued)

FOREIGN PATENT DOCUMENTS

| CN | 102922927 A | 2/2013 |
| JP | 2007159946 A | 6/2007 |

OTHER PUBLICATIONS

West Coast District Health Board, Infection Control Committee; Endoscopy Cleaning, Disinfecting and Sterilisation Procedure, WCDHB-IC0048, Version 7, pp. 1-8, Feb. 2013.
(Continued)

*Primary Examiner* — Sharidan Carrillo
(74) *Attorney, Agent, or Firm* — IP Works, PLLC; Wayne Carroll (57) ABSTRACT

A device (100) for cleaning and method of cleaning an endoscope distal end (128) is disclosed. The device (100) may include a sealed longitudinal chamber (110) that may contain a porous structure (132) with fluid, and a brush and a spring (121) loaded brush. A removable substantially airtight closure (146) may be removed to allow an endoscope distal end (128) to be placed into the longitudinal chamber (110) and contact the porous structure (132) and the brush prior to a full cleaning, thereby preventing contaminates from drying and hardening on the endoscope distal end (128) prior to a cleaning and sanitization process. The spring (121) loaded brush may be moved to clean portions of the endoscope distal end (128) including cavities such and tools including an elevator or lifter. A cap may be removed from a airtight connector (120) and a fluid source may be connected to the airtight connector (120) to assist in the endoscope (127) cleaning process.

2 Claims, 9 Drawing Sheets

(51) Int. Cl.
*A46B 5/00* (2006.01)
*B08B 1/00* (2006.01)
*B08B 9/00* (2006.01)

(52) U.S. Cl.
CPC ............... *B08B 1/002* (2013.01); *B08B 1/006* (2013.01); *B08B 9/00* (2013.01)

(56) References Cited

U.S. PATENT DOCUMENTS

| | | | |
|---|---|---|---|
| 5,168,593 A | 12/1992 | Poje | |
| 5,308,406 A * | 5/1994 | Wallock | A61L 2/18 134/42 |
| 5,443,801 A | 8/1995 | Langford | |
| 5,471,706 A | 12/1995 | Wallock et al. | |
| 5,755,894 A | 5/1998 | Bowman | |
| 7,217,684 B2 | 5/2007 | Sava | |
| 8,273,012 B2 | 9/2012 | Wallace | |
| 2003/0109837 A1 | 6/2003 | McBride-Sakal | |
| 2007/0107152 A1* | 5/2007 | Noguchi | A61B 1/122 15/104.095 |
| 2008/0251102 A1 | 10/2008 | Haack et al. | |
| 2009/0049627 A1 | 2/2009 | Kritzler | |
| 2009/0119856 A1* | 5/2009 | Onishi | A61B 90/70 15/104.066 |
| 2010/0000040 A1* | 1/2010 | Shaw | A61M 39/16 15/244.1 |
| 2011/0263933 A1 | 10/2011 | Schaaf | |
| 2012/0238816 A1 | 9/2012 | Gunday et al. | |
| 2012/0285485 A1 | 11/2012 | Majeed | |
| 2013/0276248 A1 | 10/2013 | Majeed | |
| 2013/0305469 A1 | 11/2013 | Rodriguez Sanjuan | |
| 2014/0165309 A1 | 6/2014 | Frey et al. | |
| 2017/0020380 A1* | 1/2017 | Patzek, IV | A61B 1/122 |

OTHER PUBLICATIONS http://www.infectioncontroltoday.com/articles/2008/03/scope-cleaning-and-repair.aspx; May 25, 2015.
https://ruhof.com/products/scopevalet-pull-thru-micor; ScopeValet Pull Thru Micro; May 25, 2015.
http://et-catalogue.olympus.eu/en/index.php?category=640; Single-Use cleaning brushes—combination brushes; Olympus 2013.

* cited by examiner

FIG. 9

ENDOSCOPE CLEANING BRUSH APPARATUS

RELATED APPLICATIONS

This application is related to provisional patent application U.S. 62/191,718 filed on Jul. 13, 2015, and claims international date priority thereof, and its subject matter is hereby incorporated herein by reference in its entirety.

TECHNICAL FIELD

This disclosure relates to cleaning brushes and cleaning systems for endoscopes or reusable medical devices.

BACKGROUND ART

An endoscope is an instrument used to examine the interior of a hollow organ or cavity of the body. Unlike most other medical imaging devices, endoscopes are inserted directly into the organ. Endoscopes can be used to examine and/or take samples of tissue from the interior of the body. An endoscope may have multiple channels that all generally have an opening in a region at the distal end of the endoscope. The endoscope distal end may also have instruments that move and assist in gathering samples from the interior of the body. Through the process of examination and sampling, the endoscope, and specifically the distal end with the instruments, come into contact with human tissue which may be healthy or diseased, as well as waste and body fluids.

CITATION LIST

Patent Literature

PTL 1: U.S. Pat. No. 5,755,894 (BOWMAN MICHAEL D et al.) May 26, 1998.
PTL 2: U.S. Pat. No. 8,273,012 (Wallace et al.) Sep. 25, 2012.
PTL 3: U.S. Pat. No. 5,168,593 (POJE; ALAN C. et al.) Dec. 8, 1992.
PTL 4: U.S. Pat. No. 7,217,684 (Sava et al.) May 15, 2007.
PTL 5: U.S. Pat. No. 1,742,497 (DICKINSON FAIRLEIGH S) Jan. 7, 1930.
PTL 6: United States No. 20090,049,627 (Kritzler) Feb. 26, 2009.
PTL 7: United States No. 20130,305,469 (RODRIGUEZ SANJUAN) Nov. 21, 2013.
PTL 8: United States No. 20030,109,837 (MCBRIDE-SAKAL) Jun. 12, 2003.
PTL 9: United States No. 20110,263,933 (Schaaf) Oct. 27, 2011.
PTL 10: United States No. 20130,276,248 (Majeed) Oct. 24, 2013.
PTL 11: United States No. 20120,285,485 (Majeed) Nov. 15, 2012.
PTL 12: JP 2007159946 A (Pentax Corp) Jun. 28, 2007.
PTL 13: CN 102922927 A (Ma Ronghua) Feb. 13, 2013.

Non Patent Literature

NPL 1: https://ruhof.com/product/scopevalet-pull-thru-micro, "ScopeValet™ Pull Thru™ Micro".
NPL 2: http://et-catalogue.olympus.eu/en/index.php?category=640 "Single-Use Cleaning Brushes—Combination Brushes"
NPL 3: http://www.infectioncontroltoday.com/articles/2008/03/scope-cleaning-and-repair.aspx "Scope Cleaning and Repair"
NPL 4: http://www.westcoastdhb.org.nz/publications/policies_n_procedures/policies_n_procedures_docs/infection_control/EndoscopyCleaningDisinfectionAndSterilisation Procedure.pdf "Endoscopy Cleaning, Disinfection and Sterilisation Procedure"

SUMMARY

Technical Problem

Endoscopes are not generally disposable and are re-used after a cleaning and sanitization process. When the cleaning and sanitization process is not successful at removing all contaminants, disease can be passed, and has been passed from one patient to another or multiple patients. There is a need in the art for improvements in cleaning devices and methods for cleaning endoscopes.

An endoscope may be used in a doctor's office, surgery center, wellness centers, or in a hospital such as in an operating room or other appropriate setting (together called the procedure room). Immediately after an endoscope is used, contaminates on the endoscope may still be moist and may be easier to remove than if the contaminates dry and harden. Endoscopes are used on patients, and immediately after the endoscope is used, the patient may need to be attended to, transported, or may have additional procedures performed. After the patient is attended to, the procedure room may need to be cleaned and prepared for another patient and another procedure. Therefore it is not practical in every case to begin a full cleaning process of an endoscope immediately after use.

Endoscopes need to be transported to a cleaning facility after use. During transport contaminates can become dry and may be harder to remove. During transport the instruments on the endoscope can become damaged. In some cases the most difficult portion to fully sanitize on an endoscope is the distal end, and the instruments that may be damaged are exposed at the distal end. There is a need in the art for a device that will allow safe transport to a cleaning facility, and prevent contaminants from drying on the endoscope.

Solution to Problem

After an endoscope is used, the end of the endoscope may undergo a quick and simple cleaning using a device. The device may also serve as a protector to transport the endoscope and prevent contaminants from drying on the distal end of the endoscope. A device may be provided with a longitudinal chamber with a first end, a second end, an inner surface and an outer surface, the longitudinal chamber may include an airtight connector at the second end configured to receive fluid into the longitudinal chamber. The airtight connector may include a threaded locking port for fluidly connecting the longitudinal chamber to a fluid source. The longitudinal chamber may have an opening at the first end configured to admit an endoscope distal end, wherein the longitudinal chamber comprises a cylinder.

In some embodiments the device may include a porous structure may be placed within the longitudinal chamber. The porous structure may include a hollow structure and may be adjacent to a portion of the inner surface. The porous structure may include a detergent solution.

In some embodiments the device may include a bristle brush that may have a plurality of bristles positioned within the longitudinal chamber. A portion of the plurality of bristles may be configured to contact the endoscope distal end. The bristle brush may be positioned adjacent to the second end of the longitudinal chamber.

In some embodiments the device may include a removable substantially airtight closure with a seal over the opening configured to cover the opening at the first end of the longitudinal chamber.

In some embodiments the longitudinal chamber may include a distal end receiving portion with a distal end sponge. The distal end receiving portion may include a transparent material. The distal end receiving portion may include a spring-loaded brush.

Advantageous Effects of Invention

In some embodiments the device may allow moisture and detergent to be applied to the endoscope distal end and prevent the endoscope distal end from having dried contaminants prior to a full cleaning and sanitizing process. If the endoscope distal end does have dried contaminants, the device may allow the dried contaminants to be rehydrated and therefore cleaned easier. In some embodiments the device may allow quick cleaning to remove some of the contaminants by passing the endoscope distal end over a bristle brush. In some embodiments the device may allow for further detailed cleaning of the distal end to remove contaminants from instruments on the distal end, for example the elevator (lifter) on an duoendoscope by using the spring-loaded brush.

In some embodiments additional fluid may be introduced to further clean or flush the endoscope distal end through a threaded locking port.

In some embodiments the device may allow the endoscope distal end to be transported safely so that the instruments on the distal end do not become damaged.

These and other advantages of embodiments will become more apparent upon reading the following detailed description along with the accompanied drawings.

DETAILED DESCRIPTION

FIGS. 1-4 show example embodiments of device 100 that may be placed over an endoscope distal end 128 after the endoscope 127 is used. The device 100 may be used by placing the device 100 over the endoscope distal end 128 immediately after the procedure, or before contaminates dry on the endoscope 127. The device 100 may also be used after contaminates have dried, and the device 100 may assist in removal of dried contaminates.

In some embodiments the device 100 may include a longitudinal chamber 110 with a first end 112 and a second end 114, and an inner surface 116 and an outer surface 118. The second end 114 may include an airtight connector 120. As used in this document "airtight" includes airtight, substantially airtight, and slightly airtight. An airtight structure may not prevent the flow of fluids when there is adequate pressure difference between an exterior and an interior. During storage and transport, pressure difference between the interior and exterior of the device 100 are not expected to allow fluid to pass through airtight structures. It is expected, however, that pressures during some cleaning processes when the device 100 is used, may create sufficient pressure to allow fluid to pass through airtight structures. In some embodiments some fluids may be allowed to bleed off during pressure or from the soapy scrubbing action.

In some embodiment the airtight connector 120 does not leak when in place for transport. In some embodiments the airtight connector 120 may be a luer lock connector or other type of threaded locking port 122 that allows a fluid source to be connected to the longitudinal chamber 110 in a slightly airtight manner, or in a manner that allows for little or no leakage of fluid under pressure or suction. In some embodiments the airtight connector 120 may use other types of connections to allow fluid to flow into the longitudinal chamber 110. The air tight connector may have a removable cap 156 to close the airtight connector 120. In some embodiments the airtight connector 120 may have a removable seal such as a foil seal or other type of seal so that the longitudinal chamber 110 may be filled or partially filled with a fluid while being manufactured. The fluid may include detergent, (a detergent may include enzymes or a disinfectant) and the removable cap 156 or seal may protect the fluid from drying out before use, and allow the device 100 to be stored for a one time use.

In some embodiments the airtight connector 120 may allow for some leakage so that at least a small amount of air may be drawn through the airtight connector 120 when a syringe or a mechanical suction create a vacuum, or a negative pressure in the longitudinal chamber 110. In some embodiments the airtight connector 120 may allow for at least a small amount of leakage when fluid is pumped into the longitudinal chamber 110 with a syringe or a mechanical pump, creating a positive pressure in the longitudinal chamber 110.

The first end 112 of the longitudinal chamber 110 may have an opening 126 at the first end 112 configured to admit the endoscope distal end 128. In some embodiments the longitudinal chamber 110 may be shaped as a cylinder that is round. In other embodiments the longitudinal chamber 110 may have other shapes, for example the longitudinal chamber 110 may be a square cylinder, or a cylinder with multiple sides. In some embodiments the longitudinal chamber 110 may have a diameter that allows an endoscope 127 with a width to enter the longitudinal chamber 110.

In some embodiments the longitudinal chamber 110 may include a porous structure 132 such as a sponge, felt, woven material, a combination of woven and non-woven material, or other type of material that absorbs and holds liquids. The porous structure 132 may be positioned in the longitudinal chamber 110 near or adjacent to the first end 112. In some embodiments the porous structure 132 may be shaped in a hollow structure 134 that can bend or be shaped. The hollow structure 134 may be shaped to contact a portion of inner surface 116 of the longitudinal chamber 110. In some embodiments the hollow structure 134 has a length and a width and a thickness. The length of the hollow structure 134 may be placed along a portion of the longitudinal chamber 110 with the length in the same direction as a line between the first end 112 and the second end 114. The width of the hollow structure 134 may be placed next to a portion of the inner surface 116 of the longitudinal chamber 110 and may be formed to conform to at least a portion of the inner perimeter of the longitudinal chamber 110. In some embodiments at least a portion of the hollow structure 134 is positioned in the longitudinal chamber 110. In some embodiments the hollow structure 134 has an opening 126 through the length of the hollow structure 134 that is smaller than an endoscope 127, so that when an endoscope 127 is inserted into the hollow structure 134, the porous structure 132 may be compressed and contact the endoscope 127.

The diameter of the longitudinal chamber 110 may allow for an endoscope distal end 128 to be placed in the longitudinal chamber 110 with the endoscope distal end 128 in contact with the hollow structure 134, and with the hollow structure 134 in contact with the inner surface 116 of the longitudinal chamber 110.

The porous structure 132 or hollow structure 134 may be prepared for use by placing a solution onto or into the porous structure 132 or hollow structure 134. The solution may be water, or a solution that includes detergents, including enzymes, disinfectants or a solution with other liquids. The longitudinal chamber 110 may be prepared by placing the porous structure 132 in the longitudinal chamber 110, and then closing the longitudinal chamber 110 to prevent the porous structure 132 from drying before use. The longitudinal chamber 110 may be closed by placing a removable substantially airtight closure 146, such as removable cap 156 onto airtight connector 120 at the second end 114, and by placing a removable substantially airtight closure 146 on the first end 112, such as seal. The seal may fit into opening 126 with a friction fit to create a substantially airtight seal. In some embodiments the seal may fit into opening 126 at the first end 112 with threads. In some embodiments a removable substantially airtight closure 146 may be a deformable seal that contacts the outer surface 118 and deforms to create a substantially airtight seal. In some embodiments the first end 112 may include a surface 158. The removable substantially airtight closure 146 may be a non-permeable sheet that may be removably adhered to the surface 158 so that the non-permeable sheet may cover the opening 126 at the first end 112.

A bristle brush 140 with a plurality of bristles 142 between a first point 160 and a second point 162 may be placed in the longitudinal chamber 110. The bristle brush 140 may have a length between the first point 160 and the second point 162, with at least a portion of the length of the bristle brush 140 being along a line between the first end 112 and the second end 114 of the longitudinal chamber 110. The bristles 142 may have a length and be positioned near or adjacent to the second end 114 of the longitudinal chamber 110. The length and position of the bristles 142 may allow the bristles 142 to contact at least a portion of the endoscope distal end 128 when the endoscope distal end 128 is placed into the longitudinal chamber 110. The bristles 142 may have various lengths or may all be the same lengths in different embodiments of the device 100. In some embodiments the bristles 142 may be soft bristles 142 made with a diameter and a material that will bend when the bristles 142 come into contact with the endoscope distal end 128, without damaging the endoscope distal end 128.

The hollow structure 134 may be placed to position the endoscope distal end 128 so that the endoscope distal end 128 comes into contact with the bristles 142. Endoscopes may have instruments in different places with some endoscopes having instruments facing a side direction and others may have instruments facing an end direction. The longitudinal chamber 110 may include a distal end receiving portion 115 that may include a distal end sponge 117. The distal end receiving portion 115 may include transparent material to allow a user to visually confirm that the endoscope distal end 128 is fully in position. The distal end sponge 117 may allow cleaning of surfaces, instruments, and lenses that are on the distal end face, as is the case in certain types of endoscopes and instruments. The distal end sponge 117 may include detergents, including enzymes or other fluids that may assist in cleaning the endoscope 127.

In some embodiments the hollow structure 134 may be loose within the longitudinal chamber 110. Alternatively, the hollow structure 134 may be connected to the inner surface 116 of the longitudinal chamber 110.

Bristle brush 140 may have bristles 142 that contact the side of the endoscope distal end 128. Bristle brush 140 may have bristles 142 that contact the end of the endoscope distal end 128.

Figure 10:
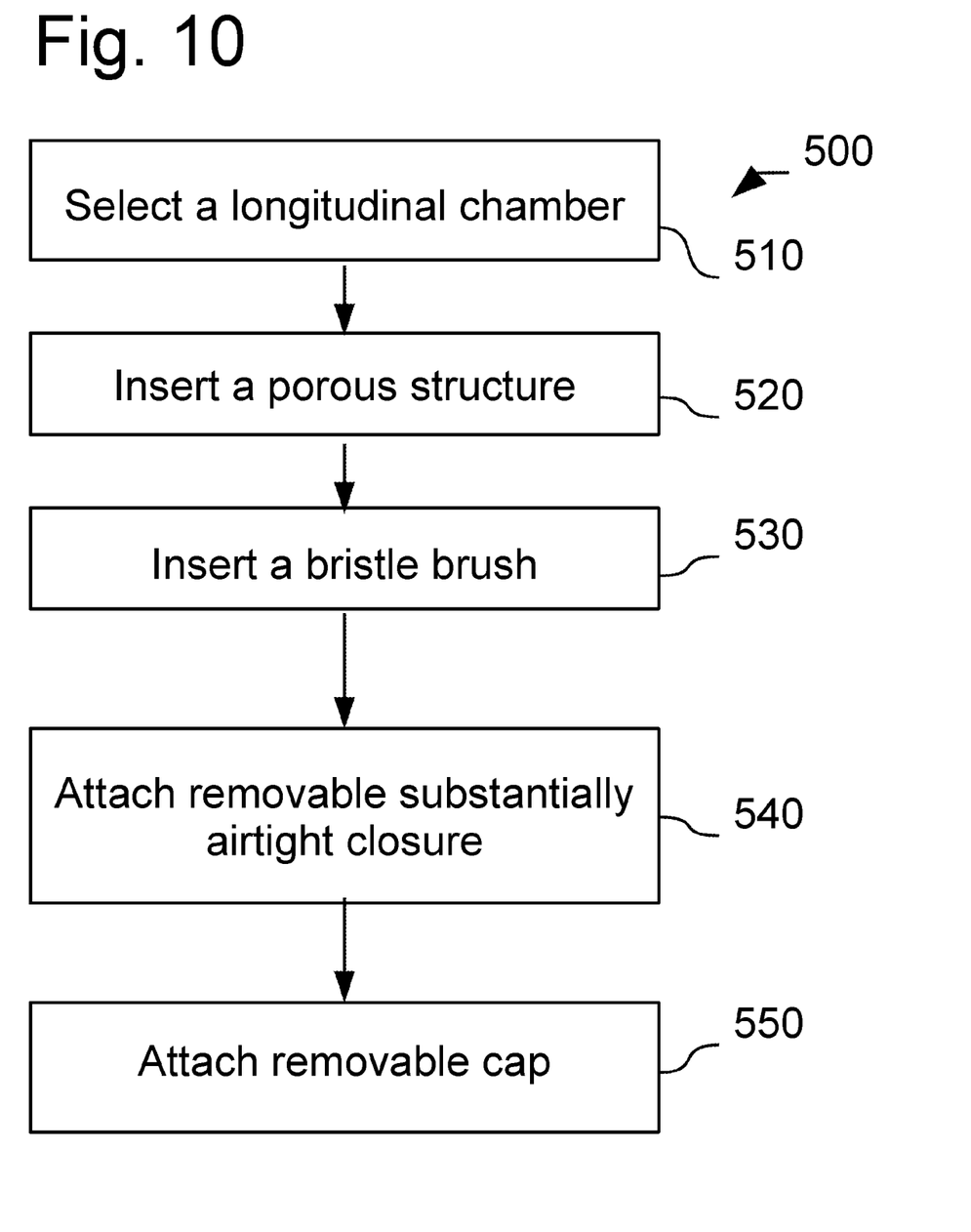
FIG. 10 is an embodiment of a method of making a device.

FIG. 10 shows an example embodiment of a method of making a device 500. In some embodiments the method of making a device 500 includes selecting a longitudinal chamber 510. As discussed above the longitudinal chamber 110 may be selected based on one or more endoscopes that can be used with the device 100.

In example embodiments the longitudinal chamber 110 may include separate parts for the first end 112 and the second end 114, with seals 154 between the center of the longitudinal chamber 110, the first end 112 and the second end 114. In other embodiments the longitudinal chamber 110 may be one part that includes the first end 112 and the second end 114 including the distal end receiving portion 115. When the longitudinal chamber 110 includes the first end 112 and second end 114 as one part, then seals 154 would not be necessary to create an air tight environment in the longitudinal chamber 110. In some embodiments the device 100 is designed to be disposable.

Another step of the method of making a device 500 may include inserting a porous structure 520 into the longitudinal chamber 110. The porous structure 132 may be configured to fit around the endoscope 127 and limit air flow around an endoscope 127 when the endoscope 127 is in place in the longitudinal chamber 110. By limiting air flow around the endoscope distal end 128, the endoscope distal end 128 may stay moist and cleaning may be more effective using the device 100. In some embodiments the porous structure 132 is impregnated with a fluid before it is inserted into longitudinal chamber 110. In some embodiments the porous structure 132 is impregnated with a fluid after it is inserted into the longitudinal chamber 110.

In some embodiments the method of making a device 500 includes inserting a bristle brush 530 into the longitudinal chamber 110. The bristle brush 140 may be inserted before the hollow structure 134 is inserted. The bristle brush 140 may be useful in cleaning structures on the endoscope distal end 128. The bristle brush 140 may be configured to be in contact with the endoscope distal end 128 when inserted into the longitudinal chamber 110. The bristle brush 140 may be useful in the cleaning process and may allow cleaning of the endoscope distal end 128 after the endoscope 127 is moved to a cleaning and sanitization area or facility.

Some embodiments include a spring-loaded brush 119 that may include a spring 121, and a brush handle 125. The distal end receiving portion 115 may include a stem 123 that supports the spring 121 and allows the spring-loaded brush 119 and brush handle 125 to move along the stem 123. The spring-loaded brush 119 may be flexible and may be at an angle relative to the position of the endoscope 127 when inserted into the device 100. The brush handle 125 may be retained on the stem 123 with end stops 129 that may be inserted or tightened after the brush handle 125 is in place. In other embodiments other methods of creating a spring 121, and allowing lateral movement of the spring-loaded brush 119 may include a flexible gasket or button, or other methods. Some embodiments of the device 100 may be made without the spring-loaded brush 119.

In some embodiments the method of making a device 500 includes attaching a removable substantially airtight closure 540 to the first end 112 of the longitudinal chamber 110. A substantially airtight closure 146 may be useful in retaining moisture inside the chamber after assembly of the device 100, and before use of the device 100. As discussed above the substantially airtight closure 146 may have different forms in different embodiments.

In some embodiments the method of making a device 500 includes attaching a removable cap 550 to the airtight connector 120. A removable cap 156 may be useful to prevent moisture from escaping the longitudinal chamber 110 before use of the device 100. A removable cap 156 may be useful to prevent moisture from escaping the longitudinal chamber 110 after the chamber is installed over an endoscope 127 and before the endoscope 127 is cleaned and sanitized.

Figure 11:
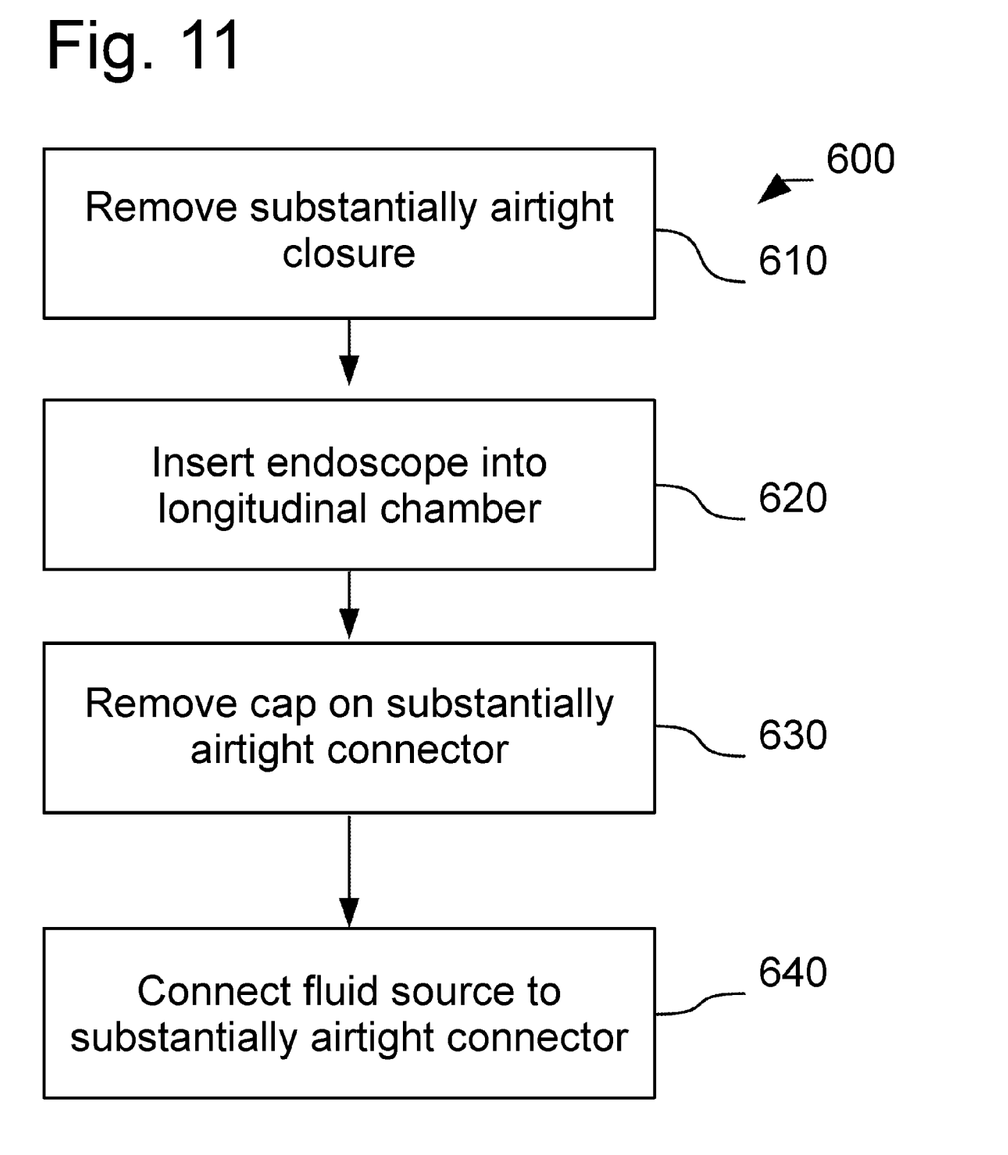
FIG. 11 is an embodiment of a method of using a device.

FIG. 11 shows an example embodiment of a method of cleaning an endoscope 600. In some embodiments the method of cleaning an endoscope 600 includes removing a substantially airtight closure 610. As discussed above, a removable substantially airtight closure 146 may be removed prior to the step of inserting an endoscope 127 into the longitudinal chamber 620. A person performing or assisting a procedure with an endoscope 127 may follow a procedure after the endoscope 127 is no longer in use on a patient, and remove the substantially airtight closure 610 on the device 100, and then quickly insert the endoscope 127 into the longitudinal chamber 620 of the device 100.

The user may move the endoscope 127 longitudinally back and forth several times partially in the device 100 to allow the fluids in the hollow structure 134 to contact the debris and contaminants on and in the endoscope 127. Moving the endoscope 127 back and forth several times may also allow the distal end to pass over the bristle brush 140 several times to loosen or remove debris and contaminants. The user may also rotate the endoscope 127 both clockwise and counter clockwise relative to the longitudinal chamber 110 while the endoscope distal end 128 is positioned between the first point 160 and the second point 162 of the bristle brush 140. A user may be able to verify that the endoscope distal end 128 is in position relative to the bristle brush 140 by looking through a clear portion of the distal end receiving portion 115.

The user may advance the endoscope distal end 128 into the distal end receiving portion 115. If the endoscope distal end 128 includes instruments on the face of the distal end, the user may rotate the endoscope 127 while contacting the distal end sponge 117 to allow detergent to assist in the cleaning process of the distal end. In some embodiments the distal end receiving portion 115 includes a spring-loaded brush 119. The user may use the brush handle 125 and while viewing the endoscope distal end 128 through the distal end receiving portion 115, advance the spring-loaded brush 119 to clean instruments on the endoscope distal end 128. The user may operate portions of the endoscope 127 to allow the flexible spring-loaded brush 119 to advance into cavities and clean portions, such as the elevator (lifter) on a duoendoscope.

Figure 1:
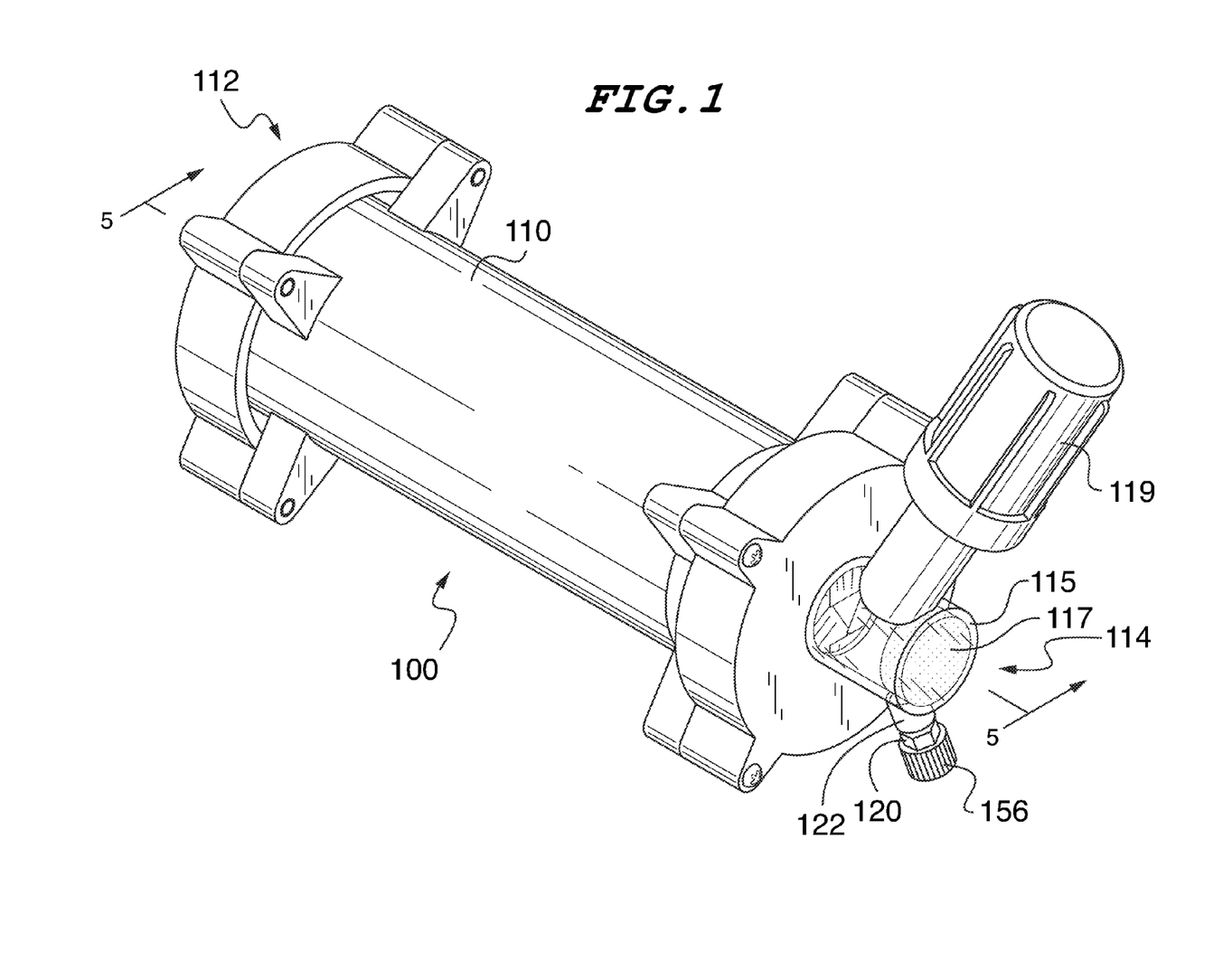
FIG. 1 is a perspective view of an embodiment of a device.
Figures 2, 3:
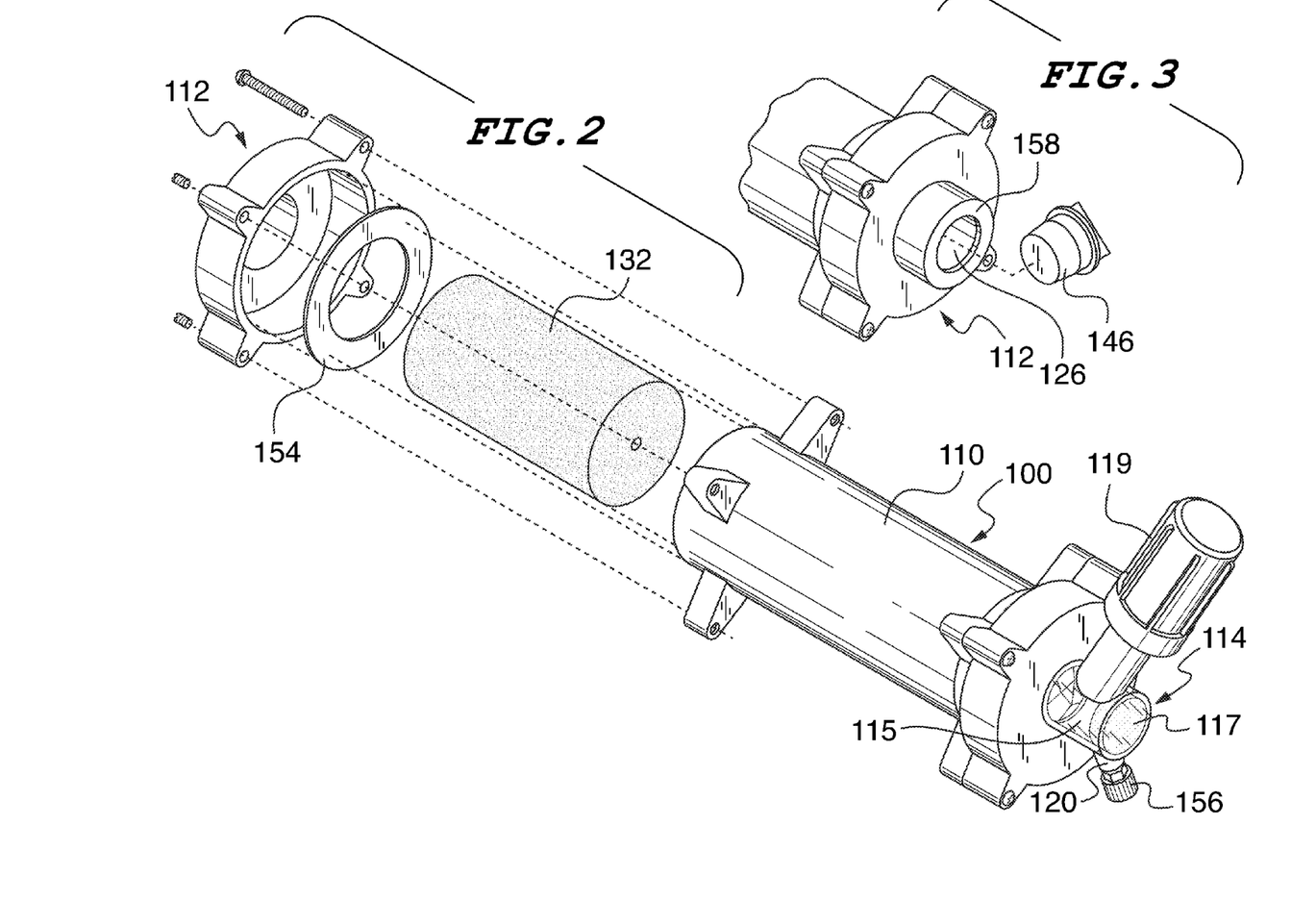
FIG. 2 is an exploded perspective view of an embodiment of a device.
FIG. 3 is a perspective view of an embodiment of a device.
Figure 4:
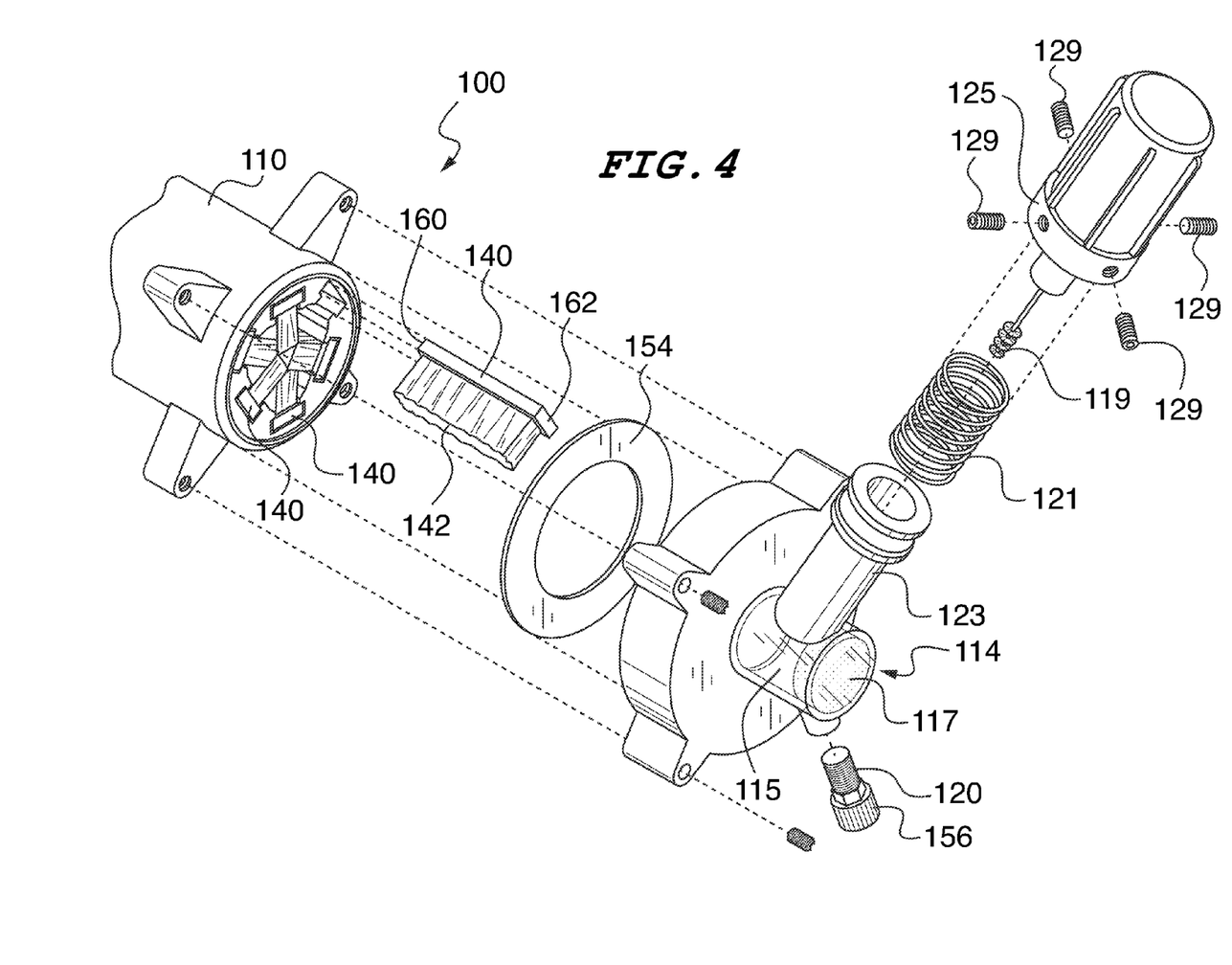
FIG. 4 is an exploded perspective view of an embodiment of a device.
Figure 5:
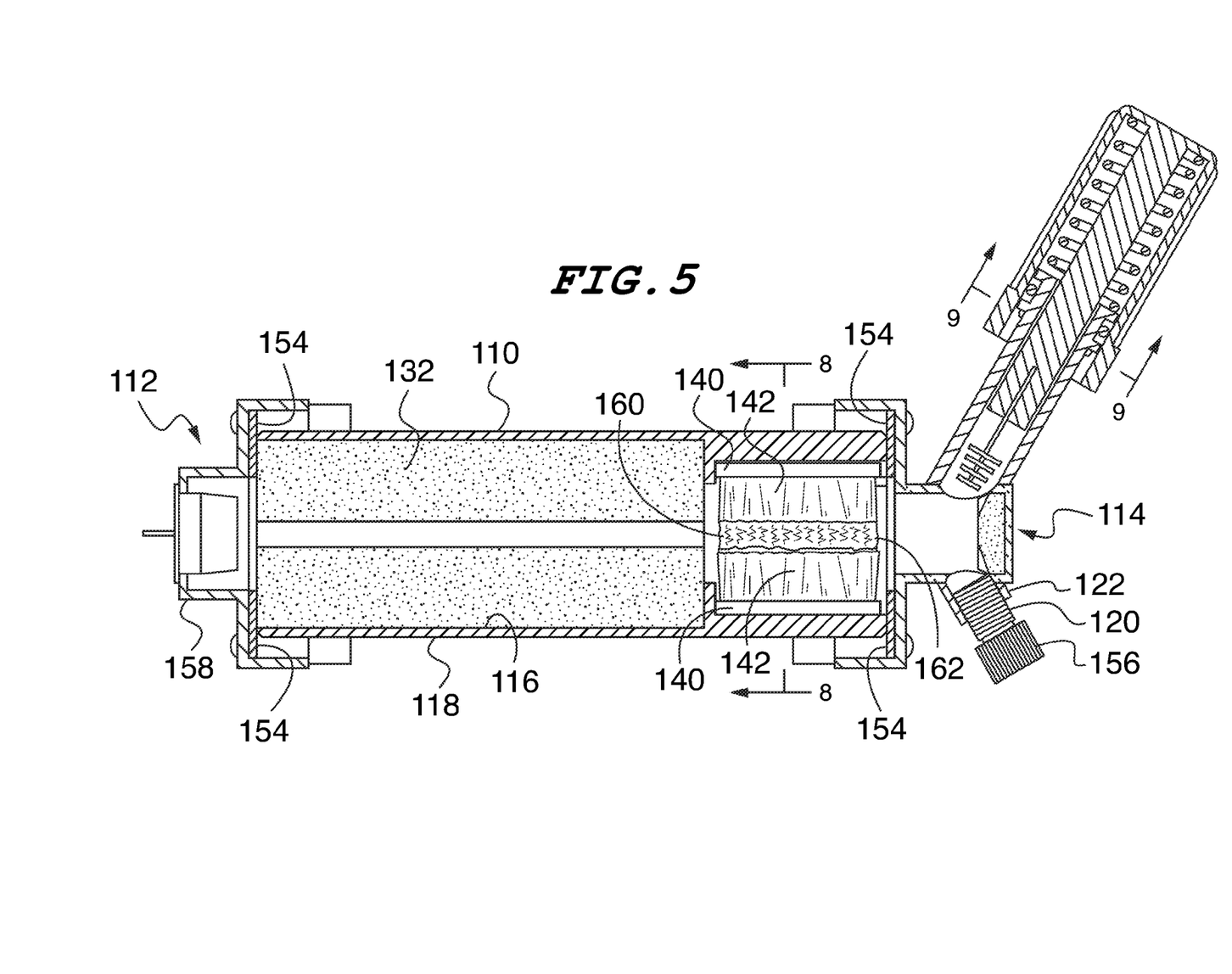
FIG. 5 is a side cut-away view along the line 5-5 from FIG. 1.
Figure 6:
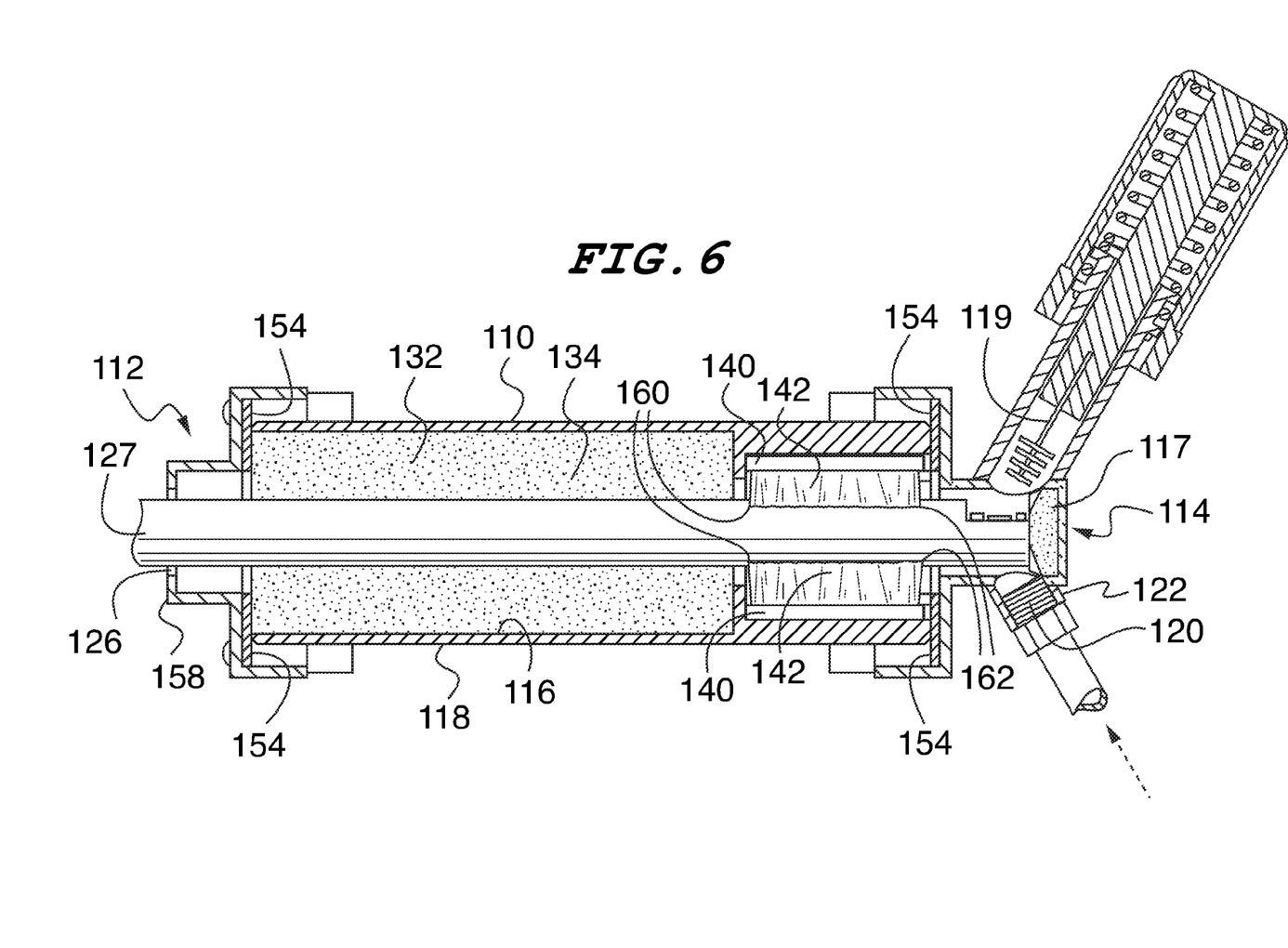
FIG. 6 is a side cut away view along the line 5-5 from FIG. 1 showing an example endoscope inserted into the device.
Figure 7:
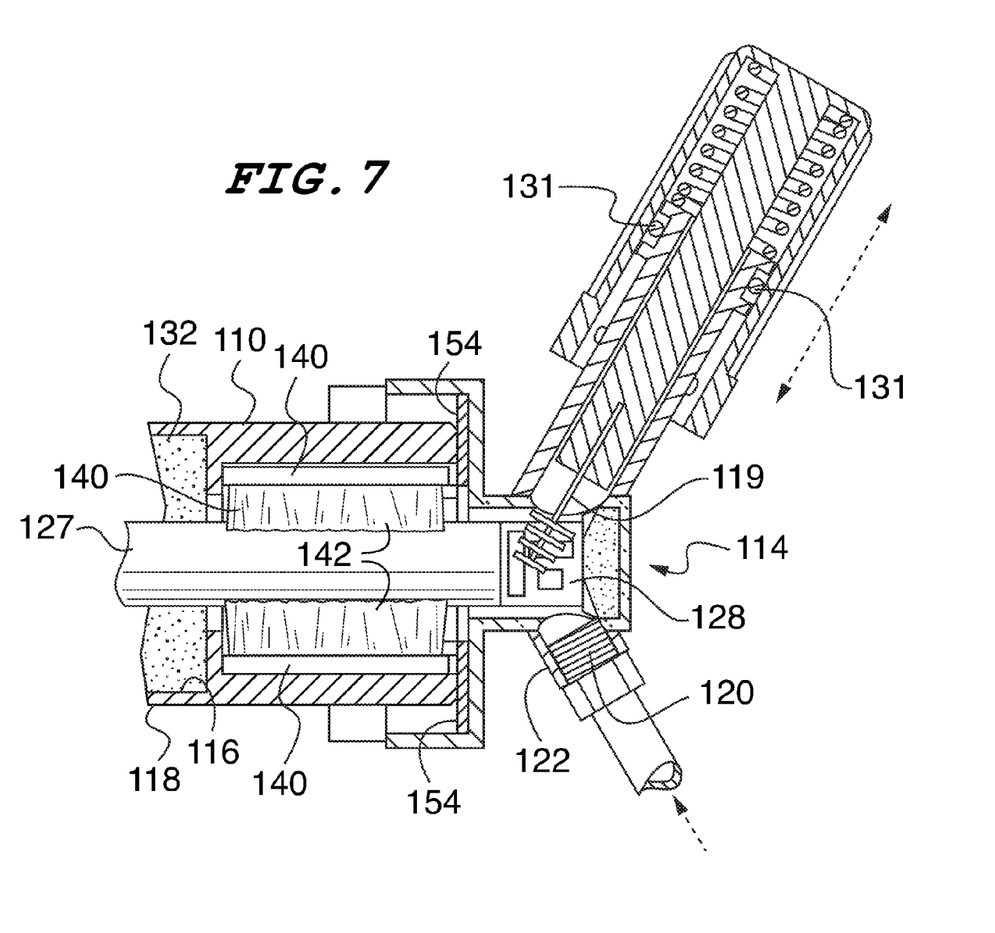
FIG. 7 is a partial side cut-away view along the line 5-5 from FIG. 1 showing an endoscope inserted into the device.
Figure 8:
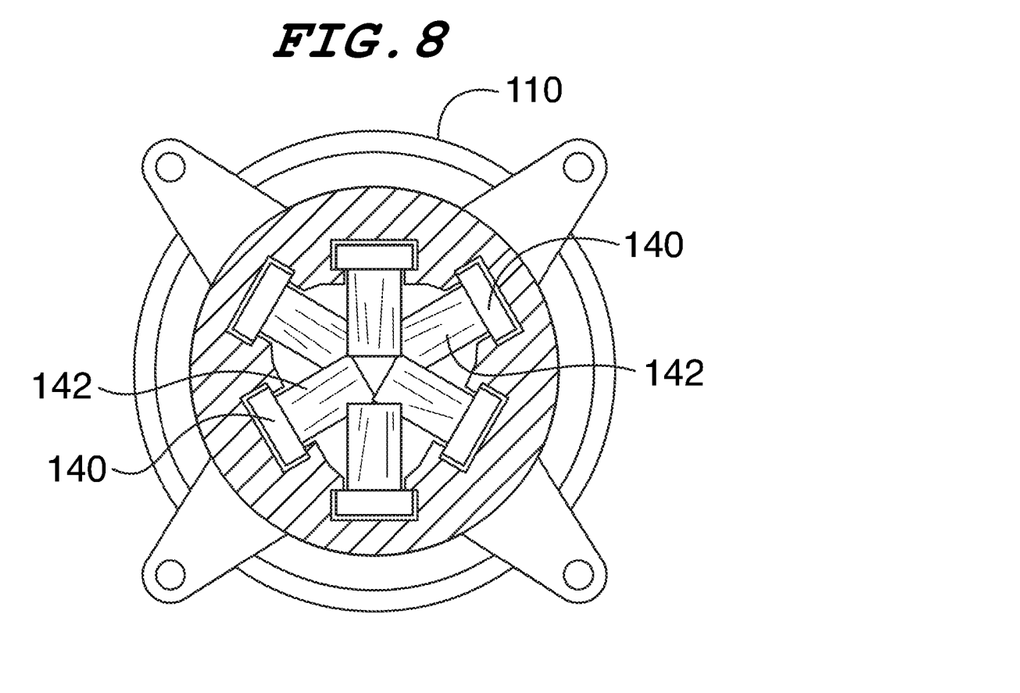
FIG. 8 is an end cut away view along the line 8-8 from FIG. 5.
Figure 9:
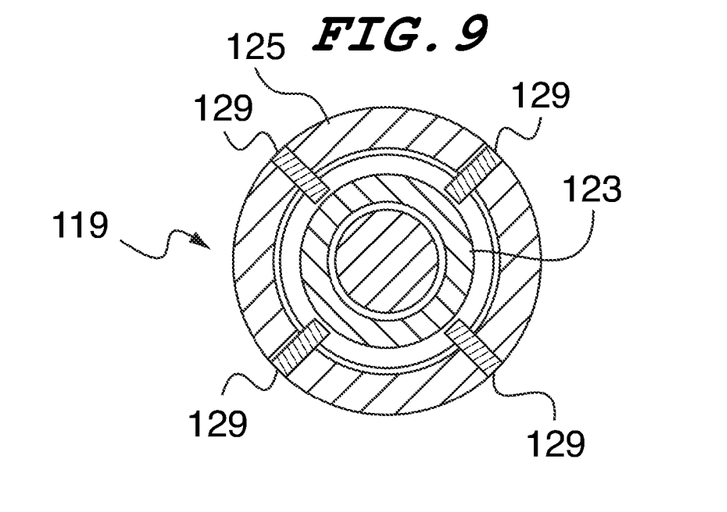
FIG. 9 is a cut away view along the line 9-9 from FIG. 5.

FIG. 7 shows the spring-loaded brush 119 in an advanced position so that it contacts the endoscope distal end 128 to allow removal of debris and contaminants. The spring-loaded brush 119 may include a handle seal 131 between the stem 123 and the brush handle 125 to prevent fluid from leaving through the spring-loaded brush 119. In other embodiments the spring-loaded brush 119 may be sealed in other ways. The removable cap 156 may be left in place with the endoscope distal end 128 in the device 100. The removable cap 156 may be removed 630 and the airtight connector 120 may be connected to a fluid source 640. In some embodiments a person assisting with a procedure using an endoscope 127 may leave the endoscope 127 cap in place until the endoscope 127 is processed for a full cleaning and sanitization. In some embodiments a person assisting with a procedure using an endoscope 127 may remove the cap on the airtight connector and attach a syringe with fluid or another fluid source and insert fluid into the longitudinal chamber 110, and then replace the cap on the airtight connector 120 so that the endoscope 127 may be cleaned and sanitized at a different time. The fluid source may include the ability to have suction (negative pressure) or pressurization (positive pressure) and may be a syringe, a mechanical pump, or connected to a source that is already pressurized such as a vacuum chamber or a pressurized fluid supply or chamber which would allow the fluids to flush debris from the internal lumens of the endoscope 127. The fluid source may also be other types of fluid sources.

While the endoscope 127 is in place in the device 100, the device 100 will protect the distal end during transport to other areas of the facilities, and may keep patient debris on the endoscope distal end 128 of the endoscope 127 from drying while waiting to be cleaned and disinfected. Hospitals and other places that endoscopes are used are often a de-humidified environment with dry moving air, which may accelerate the drying of debris. Drying of patient debris (blood, bacteria, viruses, mucus, etc) and infectious fluids makes cleaning and disinfecting of the endoscope 127 and its distal tip more difficult and can lead to patient to patient transmission of disease. The device 100 may be useful even after debris has dried on an endoscope 127, as placing the endoscope 127 into the device 100 may re-hydrate debris, and may allow detergents that may include enzymes to react with and break down debris so that the debris is easier to remove, and easier to sanitize removing all diseased material from the endoscope 127.

The bristle brush 140 may be used in the cleaning process by moving the device 100 relative to the endoscope 127 so that the endoscope 127 moves part way into and out of the longitudinal chamber 110. In some embodiments the bristle brush 140 may be used in the cleaning process by rotating the device 100 relative to the endoscope 127 with at least a partial rotation around the endoscope 127.

The device 100 may be a single use device 100 and may be discarded after use. The device 100 may be useful to protect the endoscope distal end 128 while the endoscope 127 is in transport and stored.

The disclosed device 100 may be made in various sizes to work with various types and sizes of endoscopes. For example one size of the device 100 may be for an endoscope 127 used in the lungs, also called a bronchoscope. Another size of the device 100 may be made for use with an endoscope 127 that is used for examining the large intestines, also called a colonoscope. Yet another size of the device 100 may be made for use with an endoscope 127 that is used in the small intestines, also called a duodenoscope. Other embodiments may be sized to work with other endoscopes that are now in use, or that may come into use in the future.

While the principles of the invention have been made clear in illustrative embodiments through the preceding examples, there will be immediately obvious to those skilled in the art many modifications of structure, arrangement, proportions, and methods, the elements, materials, and components used in the practice of the invention, and otherwise, which are particularly adapted to specific environments and operative requirements without departing from those principles. The appended claims are intended to cover and embrace any and all such modifications, within the limits only of the true spirit and scope of the invention.

REFERENCE SIGNS LIST

- 100 device
- 110 longitudinal chamber
- 112 first end
- 114 second end
- 115 distal end receiving portion
- 116 inner surface
- 117 distal end sponge
- 118 outer surface
- 119 spring-loaded brush
- 120 airtight connector
- 121 spring
- 122 threaded locking port
- 123 stem
- 125 brush handle
- 126 opening
- 127 endoscope
- 128 endoscope distal end
- 131 handle seal
- 132 porous structure
- 134 hollow structure
- 140 bristle brush
- 142 bristles
- 146 airtight closure
- 154 seals
- 156 removable cap
- 158 surface
- 160 first point
- 162 second point
- 500 method of making a device
- 510 selecting a longitudinal chamber
- 520 inserting a porous structure
- 530 inserting a bristle brush
- 540 attaching a removable substantially airtight closure
- 550 attaching a removable cap
- 600 method of cleaning an endoscope
- 610 removing a substantially airtight closure
- 620 inserting an endoscope into the longitudinal chamber
- 630 removing the cap on the airtight connector
- 640 connecting to a fluid source

What is claimed is:

1. A method of cleaning an endoscope distal end with a device, the device comprising:
    a longitudinal chamber with a first end and a second end, with an airtight connector at the second end configured to receive fluid into the longitudinal chamber, wherein the longitudinal chamber has an opening at the first end;
    a porous structure within the longitudinal chamber;
    a bristle brush with a first point and a second point, and a plurality of bristles positioned between the first point and the second point within the longitudinal chamber; and
    a spring-loaded brush comprising a spring and a brush handle having bristles, said spring-loaded brush connected at an angle to the second end of the longitudinal chamber; the method comprising:
        receiving fluid in the second end of the longitudinal chamber;
        inserting the endoscope distal end into the longitudinal chamber through the opening at the first end and passing the endoscope distal end past the second point of the bristle brush, with the endoscope distal end in contact with at least a plurality of bristles; and
        moving the spring-loaded brush at said angle to clean the endoscope distal end, wherein the spring-loaded brush moves along a stem positioned in the second end of the longitudinal chamber.

2. The method of claim 1 further comprising:
    connecting a fluid source to the airtight connector to provide said fluid to the second end of the longitudinal chamber.

* * * * *